(12) United States Patent
Beecher

(10) Patent No.: US 7,820,963 B2
(45) Date of Patent: Oct. 26, 2010

(54) METHOD FOR GENERATION AND USE OF ISOTOPIC PATTERNS IN MASS SPECTRAL DATA OF SIMPLE ORGANISMS

(75) Inventor: Christopher William Ward Beecher, Ann Arbor, MI (US)

(73) Assignee: Metabolic Alayses, Inc., Chapel Hill, NC (US)

( * ) Notice: Subject to any disclaimer, the term of this patent is extended or adjusted under 35 U.S.C. 154(b) by 114 days.

(21) Appl. No.: 12/186,381

(22) Filed: Aug. 5, 2008

(65) Prior Publication Data

US 2009/0039246 A1 Feb. 12, 2009

Related U.S. Application Data

(60) Provisional application No. 60/976,923, filed on Oct. 2, 2007, provisional application No. 60/954,253, filed on Aug. 6, 2007.

(51) Int. Cl.
*B01D 59/44* (2006.01)
(52) U.S. Cl. .................. 250/282; 250/281; 250/288; 435/6; 435/41; 435/42; 436/15; 436/19; 436/56
(58) Field of Classification Search .................. 250/281, 250/282, 288, 301, 304; 506/10, 12–22, 506/25–27, 33, 35, 43; 435/6, 41, 42, 173.1, 435/173.2; 436/15, 19, 56; 514/2, 44 A
See application file for complete search history.

(56) References Cited

U.S. PATENT DOCUMENTS

| 5,087,815 A * | 2/1992 | Schultz et al. ............. 850/63 |
| 5,462,946 A * | 10/1995 | Mitchell et al. ............. 514/315 |
| 5,912,178 A * | 6/1999 | Porter et al. ................ 436/55 |
| 6,355,416 B1 * | 3/2002 | Abramson .................... 435/6 |
| 6,849,396 B2 * | 2/2005 | Schneider .................... 435/4 |
| 6,940,065 B2 * | 9/2005 | Graber et al. ................ 250/282 |
| 6,952,818 B2 * | 10/2005 | Ikeuchi ........................ 430/311 |
| 7,045,296 B2 * | 5/2006 | Parker et al. ................. 435/7.1 |
| 7,368,710 B2 * | 5/2008 | Garner et al. ............... 250/283 |
| 2004/0091943 A1 * | 5/2004 | Schneider .................... 435/7.1 |
| 2007/0275483 A1 * | 11/2007 | Liotta et al. ................. 436/536 |

(Continued)

OTHER PUBLICATIONS

Hellerstein, *Metabolic Engineering* 6:85-100 (2004).

(Continued)

*Primary Examiner*—Bernard E Souw
(74) *Attorney, Agent, or Firm*—Husch Blackwell Welsh & Katz

(57) ABSTRACT

A method for identifying a biological analyte that is affected by a stressor is disclosed in which two substantially identical biological samples are provided, with a first sample being a control sample and a second sample being an experimental sample. The control sample is grown with a nutrient having an isotope of a first atom, whereas the experimental sample is grown with a nutrient having a second isotope of the first atom. The experimental sample is grown with a stressing agent and regimen. The samples are admixed, and the formed composite is mass spectroscopically assayed for analyte peaks. The ratio of first isotope to second isotope is determined for the peaks, as is a sample median isotopic ratio. The ratio for assayed analyte peaks is compared with the median ratio. An analyte whose isotopic ratio significantly deviates from the median ratio is an analyte affected by the stressing agent.

16 Claims, 5 Drawing Sheets

U.S. PATENT DOCUMENTS

2009/0039247 A1* 2/2009 Beecher .................. 250/282
2009/0124518 A1* 5/2009 Beecher .................. 506/22

OTHER PUBLICATIONS

Williams et al., *Experimantal Cell Research* 69:106-112 . (1971).

Wu et al., *Anal Biochem* 336:164-171 (2005).

Katajamaa et al., BMC *Bioinformatics* 2005, 6 : 179 doi:10.1186/1471-2105-6-179.

Rögnvaldsson et al., 2004 *J. Chrom. B*, 807:209-215; doi:10.1016/j.jchromb.2004.04.010.

Johannsen, 1911 *American Naturalist* 45:129-159.

\* cited by examiner

METHOD FOR GENERATION AND USE OF ISOTOPIC PATTERNS IN MASS SPECTRAL DATA OF SIMPLE ORGANISMS

CROSS-REFERENCE TO RELATED APPLICATION

This application claims benefit of Provisional Patent application No. 60/954,253, entitled "A method for the production and use of mass spectral standards" filed on Aug. 6, 2007, and Provisional Patent application No. 60/976,923 entitled "Method for the generation and use of isotopic patterns in mass spectral data" filed on Oct. 2, 2007, which are hereby incorporated by reference.

TECHNICAL FIELD

The present application relates to the creation and use of isotopic patterns in mass spectral analyses. These patterns can be introduced through either biological or non-biological methods, or combinations of both. More specifically, the isotopic patterns can be used in biological systems to determine the biochemical response of a living organism to a physical, physiological, chemical, or externally induced stressor.

BACKGROUND ART

The use of stable isotopes for the determination of biological information has a long and illustrious history [see, Hellerstein, *Metabolic Engineering* 6:85-100 (2004)]. The oldest and most frequent such usage is in studies probing metabolism wherein a stable isotope is incorporated into a specific molecule at a specific location. This isotopically-labeled molecule, or "precursor", is fed to an in vivo organism, in vitro cell system, or in vitro cell-free system for either a brief or extended period of time, after which the fate of the isotope is determined, either by use of NMR, mass spectrometry (MS), chemical degradation, or other detection technique.

In contrast to the use of radioactive isotopes, the use of stable isotopes is generally regarded as safe and free of regulation. Although in general, a study typically uses a single isotope incorporated into a specific location in order to achieve a precision in understanding the metabolic fate of a molecule, another embodiment of the use of stable isotopes utilizes wholly-labeled molecules (>99% of an atom is replaced with an isotopic equivalent), or universally-labeled (the isotope is universally distributed within the target molecule at less than saturation levels). There are many known studies in which more than one isotope is incorporated into a target molecule, and all of the isotopic fragments are examined for their differential fates. In all cases, these methods are targeted analyses; i.e., they seek the incorporation of a specific labeled atom into other specific molecules.

Yet another use of stable isotopically labeled compounds is as internal standards for their non-labeled counterparts. In such an experiment an isotopically enriched molecule is added to a sample or extract at a known concentration prior to an analysis, and the final measurement determines the exact concentration of the non-labeled material by comparison. In this type of study, it is not uncommon for a researcher to add more than one isotopically-distinct standard if more than one molecule is to be quantified. Indeed, there are extreme forms where one prepares an extremely complex mixture by growing a complex organism on an isotopically-defined feedstock such that the entire organism is heavily, if not entirely, composed of molecules consisting of only one isotope [Wu et al., *Anal Biochem* 336:164-171 (2005)]. In this situation, the same standard is introduced into all samples, but there is no information carried by the standard other than for purposes of relative quantitation; i.e., the standard has no relation to the experiment at hand. Historically, such standards are carefully constructed to differ from any other analyte by a specific mass difference.

BRIEF SUMMARY OF THE INVENTION

In one aspect, the present invention contemplates a method for identifying an analyte of a biological sample that is affected by a stressor. That method comprises the steps of providing a composite biological organism sample that is comprised of two admixed substantially identical samples of biological organisms that are a control sample and an experimental sample. The control sample organisms had been grown in a first nutrient medium containing predetermined amounts of first and second isotopes of a first atom within a nutrient, whereas the experimental sample was grown in a second nutrient medium substantially identical to the first nutrient medium but containing different predetermined amounts of the first and second isotopes of that first atom within the nutrient compared to said first nutrient medium. The first and second isotopes are other than H or D.

The experimental sample is cultured with a stressing regimen containing a stressing agent for a time period sufficient for the sample to grow and the control sample is cultured for the same period of time with a regimen substantially identical to the stressing regimen but lacking the stressing agent. The stressing agent may be chemical, genetic, environmental, or any element or combination of elements that induce physiological alteration. The composite biological organism sample is mass spectroscopically analyzed for analyte peaks. The ratio of first isotope to second isotope for each analyzed analyte peak is determined. The composite biological organism sample median isotopic ratio is determined. The ratio of first isotope to second isotope for each analyzed analyte peak is compared with the composite biological sample median isotopic ratio, and an analyte whose isotopic ratio significantly deviates from the composite biological sample median isotopic ratio is an analyte affected by the stressing agent.

Another aspect of this invention contemplates another method for identifying an analyte of a biological sample that is affected by a stressor. That method comprises the steps of providing two substantially identical biological samples, a first sample that is a control sample and the second sample that is an experimental sample. The control sample is conditioned in a first composition containing predetermined amounts of first and second stable isotopes of a first atom within a nutrient, and the experimental sample is conditioned in a second, substantially identical, composition containing different predetermined amounts of those first and second stable isotopes of that first atom within that nutrient. The first and second isotopes are other than H or D. The word "conditioned" is used herein to mean grown for a few cycles in the absence of stressor compound.

The experimental sample is grown in the second nutrient medium with a stressing regimen containing a stressing agent. That stressing regimen is maintained for a time period sufficient for the experimental sample to grow. The control sample is grown in the first nutrient medium with a regimen substantially identical to the stressing regimen used for the experimental sample, but lacking the stressing agent. The regimen is maintained for a time period sufficient for the control sample to grow.

The two samples are admixed, preferably in substantially identical amounts, to form a composite biological sample.

The composite biological sample so formed is mass spectroscopically analyzed for analyte peaks. The ratio of first isotope to second isotope is determined for the analyzed analyte peaks. A median isotopic ratio is determined for the composite biological sample. The ratio of first isotope to second isotope for each analyzed analyte peak is compared with the composite biological sample median isotopic ratio. An analyte whose isotopic ratio significantly deviates from the composite biological sample median isotopic ratio is an analyte affected by the stressing agent.

BRIEF DESCRIPTION OF THE DRAWINGS

In the drawings forming a portion of this disclosure.

Figure 1:
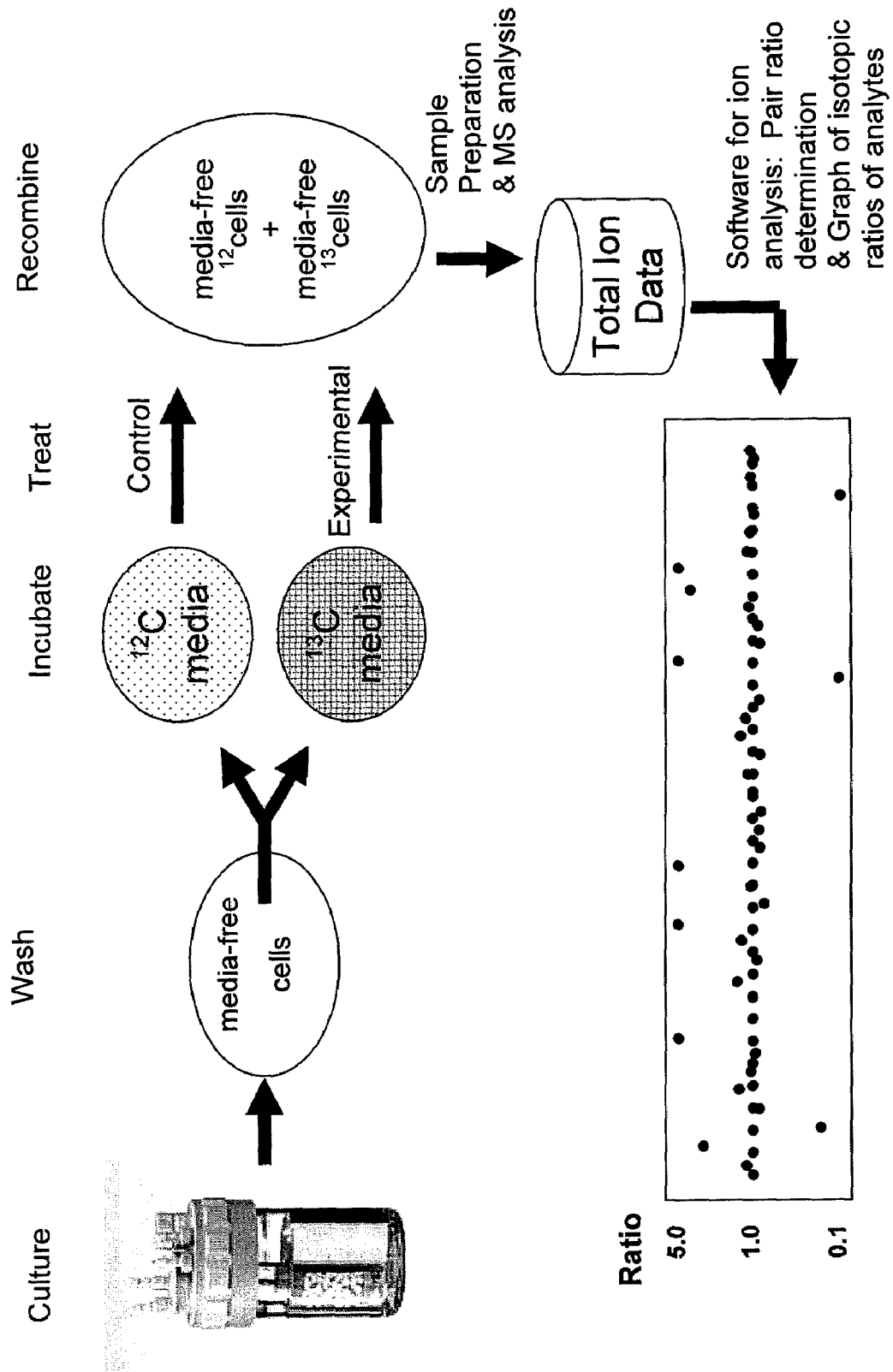
FIG. 1 is a schematic illustration of the methodology utilized herein. Thus, matched cell samples are introduced into isotopically defined media whereupon they are permitted to grow before being subjected to the experimental stressing treatment. After separation of the cells from their media, a composite sample is created by admixing one control sample and one experimental sample. The composite samples are processed, chromatographed, and mass spectroscopically analyzed as single samples. The total ion current derived from the composite sample is analyzed for peaks representing isotopic variant compounds. Each compound is represented by two peaks or isotopic forms; one each from the control and experimental conditions respectively. The ratio of the two peaks associated with each compound is determined and typically graphed. Outliers to the average ratio are compounds whose biochemistry is disturbed as part of the stress.
Figure 2:
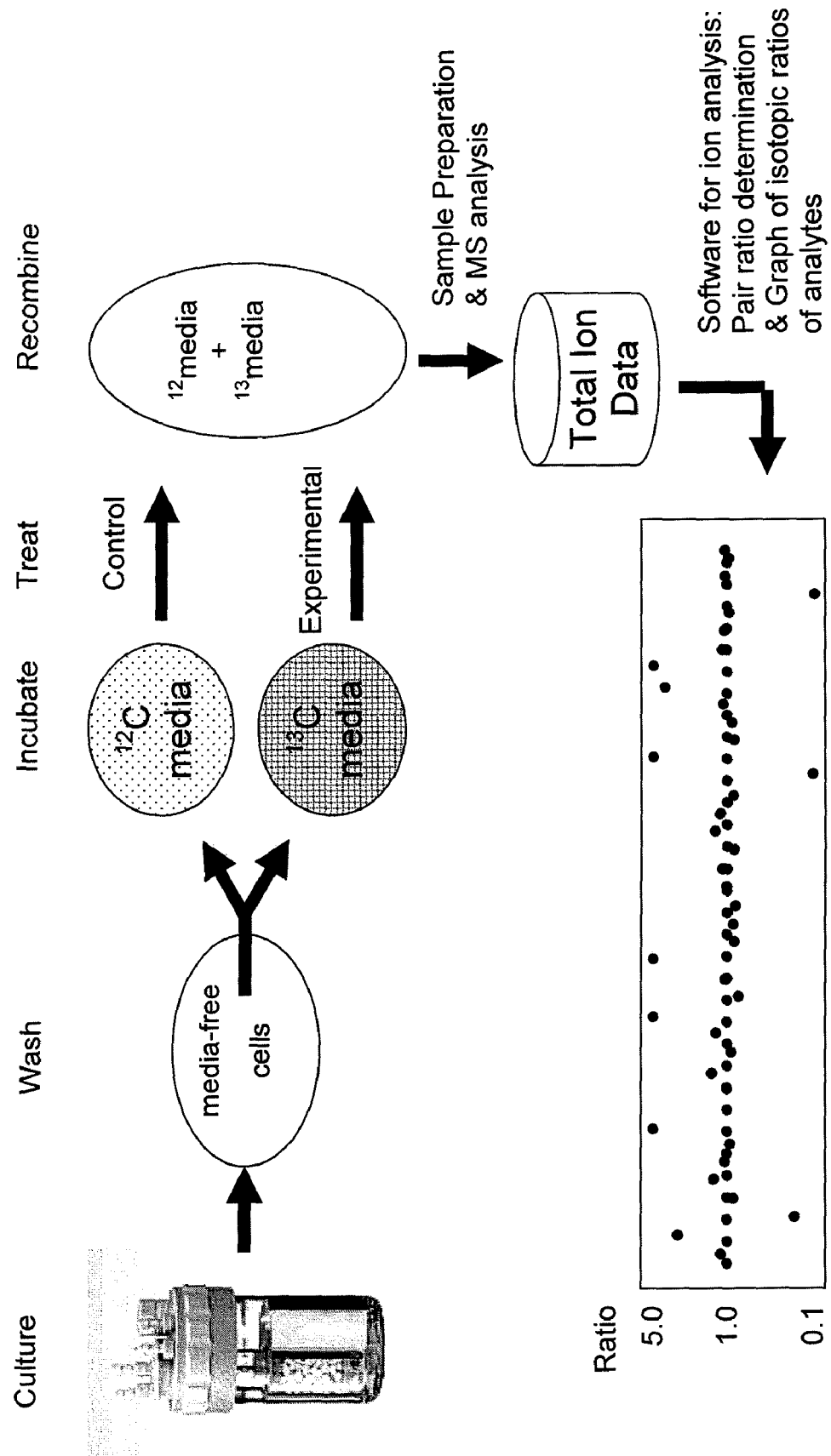
FIG. 2 is a schematic that illustrates the methodology of the invention in which it is not the cell contents that are analyzed but rather the media in which the cells have been grown.

The present invention has several benefits and advantages.

One benefit is that by the use of specifically designed isotopic ratios one can identify the source of analyte peaks seen in the spectrum, irrespective of spectral complexity. Specifically, a spectral signal can a) originate from the control culture, or b) experimental culture, or c) be an artifact acquired during sample preparation, or d) originate from the externally applied drug or response inducer, or standard. Each of these classes of compounds has unique characteristics.

One advantage of the invention is that experimental variation that is experimentally introduced; i.e., "noise", is statistically nullified and/or greatly minimized.

Another benefit of the invention is that at the liquid chromatography-mass spectral interface, there is a loss of signal due to "ion suppression". Ion suppression occurs whenever there is more compound than charge availability. In this situation, some compounds become charged at the expense of other compounds. The variability of ionization efficiency is such that some molecules cannot be accurately quantified. The present method almost fully removes the problem of ion suppression because a compound's ability to ionize is a function of its structure and is not significantly altered by its isotopic distribution.

Still further benefits and advantages of the invention will be apparent to the skilled worker from the disclosure that follows.

DETAILED DESCRIPTION OF THE INVENTION

In one aspect of this invention, the metabolic capacity of a living system is used to explore the impact of a stressor on that system by comparing its biochemical response to that of an un-treated control, directly and within a single sample. The method uses a specific experimental design and universally distributed isotopic incorporations to establish baseline responses for each system in a normal (or "control"), and one or more experimental (treated, or otherwise "stressed") system(s).

As used herein, a "stressor" can be any thing that causes or could cause a change in a living organism. Exemplary stressors include a drug, hormone, temperature, ionizing and non-ionizing radiation and the like. The word "drug" is meant to include an externally (exogenously) supplied chemical substance that upon absorption into a cell, alters the function of the cell in some manner. As such, a compound such as an exogenously supplied vitamin, mineral, toxin, antagonist, or agonist can be deemed to be a "drug". Dietary minerals are the chemical elements required by living organisms, other than the four elements carbon, hydrogen, nitrogen, and oxygen that are present in common organic molecules. Dietary minerals are often classified as "macromineral" or "microminerals" (or "trace minerals") and are usually required in greater or lesser amounts by an organism.

Hormones are defined as being internally (endogenously) supplied materials that alter the function of a cell in some manner. A hormone that is supplied to a cell from a source external to the cell is still considered a hormone herein.

Thus, control sample organisms are grown in a first nutrient medium containing predetermined amounts of first and second stable isotopes of a first atom within a nutrient. The experimental sample organisms are grown in a second nutrient medium substantially identical to the first nutrient medium, but containing different predetermined amounts, compared to said first nutrient medium, of the first and second stable isotopes of that first atom within the nutrient.

Illustratively for a system using stable isotopes of carbon [carbon-12 ($^{12}C$) and carbon-13 ($^{13}C$)], the isotopic ratios in this example specifically include a dilution of five to ten percent of one carbon isotope in another; i.e., one sample is grown on a carbon source (nutrient in a medium) that can be 95% carbon-12 ($^{12}C$) and 5% carbon-13 ($^{13}C$), hereinafter called "C-12 medium", and in such a situation the other sample is grown in mirrored medium that contains a nutrient that contains 95% carbon-13 and 5% carbon-12 in a medium, hereinafter called "C-13 medium". In each of these cases the biological system takes up the nutrient in the medium and grows upon it in such a way as to transform itself so that all of its parts are distinctively identifiable as to their origin. Further information can sometimes be obtained by incorporating a second set of two isotopes of a second atom present at two different predetermined isotopic ratios into the nutrient compositions.

As used herein, predetermined first and second stable isotope amounts are preferably present in "inverted ratios" of each other such as those discussed immediately above in which the number of the numerator of the first ratio is the number of the denominator of the second ratio, and the number of the denominator of the first ratio is the number of the numerator of the second ratio. Taking the above ratios of 95% and 5%, a first ratio would be 95/5 $^{12}C/^{13}C$ in the C-12 medium, whereas the second, inverted ratio, would be 5/95 $^{12}C/^{13}C$ in the C-13 medium. It is to be understood that a contemplated set of preferred ratios need not be 95/5 and 5/95 and that those numbers are just used for convenience. It is preferred that neither isotopic ratio is the naturally occurring ratio.

Experimental variance or "noise" is a fact of any experimental design. Because experimental variance or noise is so prevalent, experiments are often required to be performed with a large number of replicates in order to be assured that the true signal may be discriminated from artifactual (or statistical) noise. In the current "Design of Experiments" literature the sample population size needed to achieve a given power is specifically calculated from the amount of expected variance in the sample set. Therefore, any reduction in sample variance (or "noise") reduces the number of samples required to determine a given effect. The sources of variance are the result of 1) uncontrollable differences in the sample (for instance: sourcing, growth, development, handling, processing, etc.), 2) uncontrolled differences in the analytical process (for instance: materials, handling, processing, timing, etc.), or 3) errors introduced during the informatic analysis (for instance: randomness errors, algorithm errors, hardware errors, etc.). This invention reduces these sources of variance by:

1) removing pre-experimental, or "source-based", variance by establishing all samples from a single source, and holding this source constant for the duration of the experiment;

2) removing post-experimental (analytical, or informatics-based) variance by combining the material content of the experimental and control samples into a single composite sample. There can therefore no longer be variation introduced by sample handling because what happens to the control sample also happens to the experimental sample.

In order to combine the samples, the samples are uniformly and universally labeled with appropriate isotopes. An element in which there are two stable isotopes that are not significantly distinguished by enzymes or living systems can be used. Carbon (specifically, $^{12}C$ and $^{13}C$) is used for purposes of illustration herein because of its universal applicability; however, additional examples include the isotopes of nitrogen ($^{14}N$ and $^{15}N$), oxygen ($^{16}O$, $^{17}O$, or $^{18}O$), sulfur ($^{32}S$, $^{33}S$, $^{34}S$, or $^{36}S$), chlorine ($^{35}Cl$ and $^{37}Cl$), magnesium ($^{24}Mg$, $^{25}Mg$ and $^{26}Mg$), silicon ($^{27}Si$, $^{28}Si$ and $^{29}Si$), calcium ($^{40}Ca$, $^{42}Ca$, $^{43}Ca$, and $^{44}Ca$), and bromine ($^{79}Br$ and $^{81}Br$)

The use of isotopes that exhibit minimal biological isotope effect is of import. For instance, the use of the isotopes of hydrogen (D or T, which is radioactive and thus not favored) would not be suitable because they frequently cause an observable effect on metabolism due to the fact that the deuterium isotope has a mass that is twice that of hydrogen, and thus, is known to cause a reduction in the kinetics of some enzyme mechanisms but not in as an illustrative element for incorporation and use others. The discussion that follows considers carbon in an assay. However, there are examples where other elemental combinations can provide less broad but specific insights.

Compounds of biological origin are unique in that they are all interrelated through the biological process. A contemplated method extends this truth by creating two populations of almost identical biological potential but requiring that each be based on differing isotopic source material. Thus, each biological sample has a full biochemical complement that is made up of differing isotopic distributions. In the simplest case, two classes of samples are created, e.g. experimental and control. One of these classes, for the sake of this discussion the "control", is derived from medium in which the isotopic distribution was primarily carbon twelve and the other (the "experimental") is based on medium that was primarily carbon thirteen.

When these two samples are mixed, intermingled or otherwise composited, the composite sample contains molecules from both the "control" (that are made up of a substantial majority; i.e., 90% to 95%, of $^{12}C$) and the "experimental" (that are made up of a substantial majority; i.e., 90% to 95%, of $^{13}C$). Using the mass distribution for all of compounds identified from such a composite sample one can determine the relative contributions for each compound from either original sample.

Figure 3:
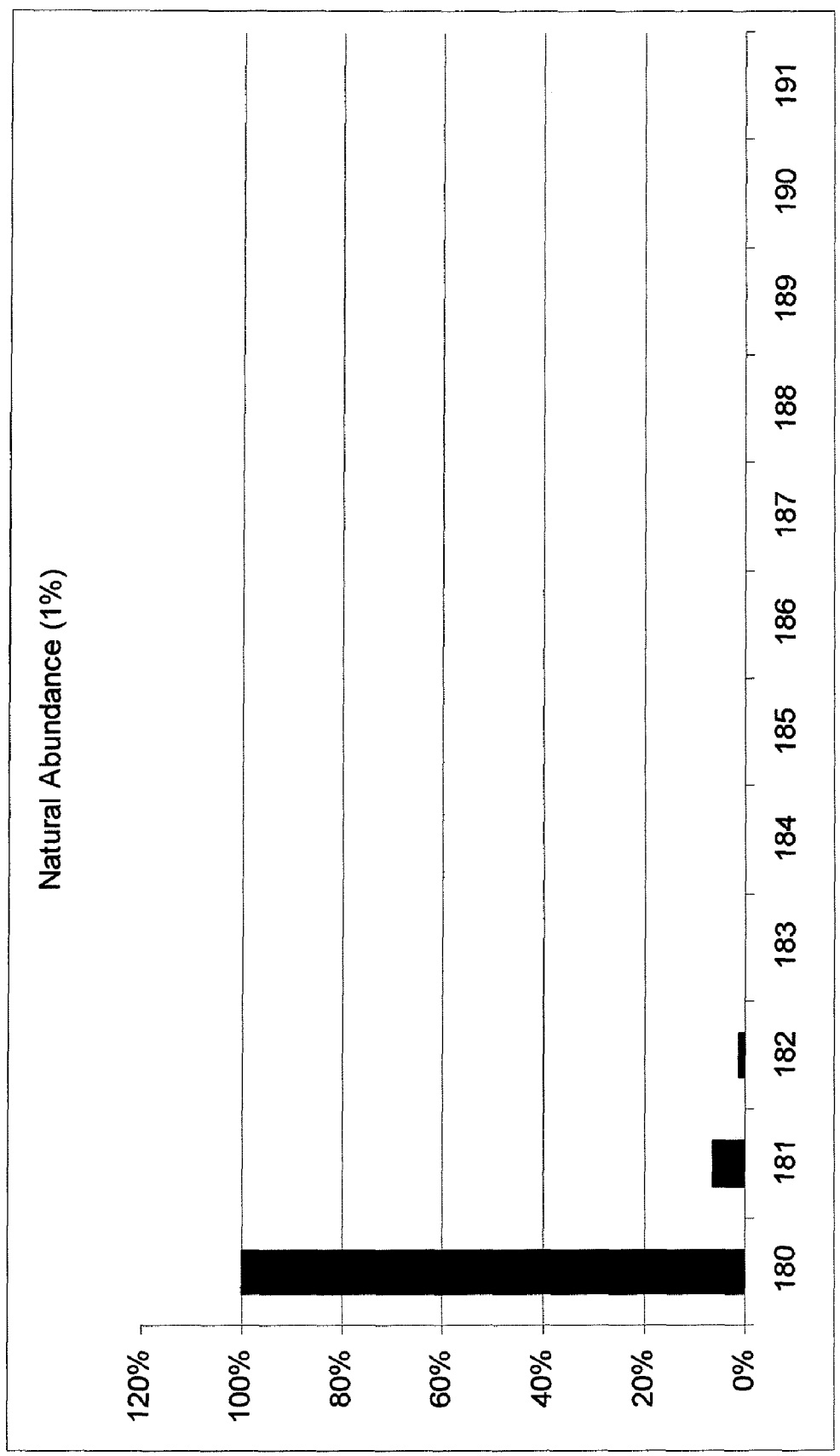
FIG. 3 illustrates a hypothetical mass spectrum obtained by analyzing natural abundance C-12 (98.9% C12) glucose with an equivalent amount of C-13 (98.9% C-13) glucose.

Deviating significantly from the 90% to 95% ratio taught by this method reduces the potential for interpretation. Consider three cases for isotopic ratios; 1) the natural abundance of $^{12}C$ is approximately 98.9%, whereas the natural abundance of $^{13}C$ is approximately 1.1%, 2) nearly pure (i.e. approaching 100%) of each, or 3) controlled isotopic ratio mixtures. In case 1, natural abundance, every compound will be a collection or mixture of isotopomers that vary in mass due the presence of $^{13}C$ impurity in the $^{12}C$ background (see FIG. 3). Thus, the distribution of these isotopomers as seen in the mass spectrometer will include a number of peaks derived from ions (also called "daughter") that are shifted up to higher mass from the peak (also called "parent") of the majority ion.

Figure 4:
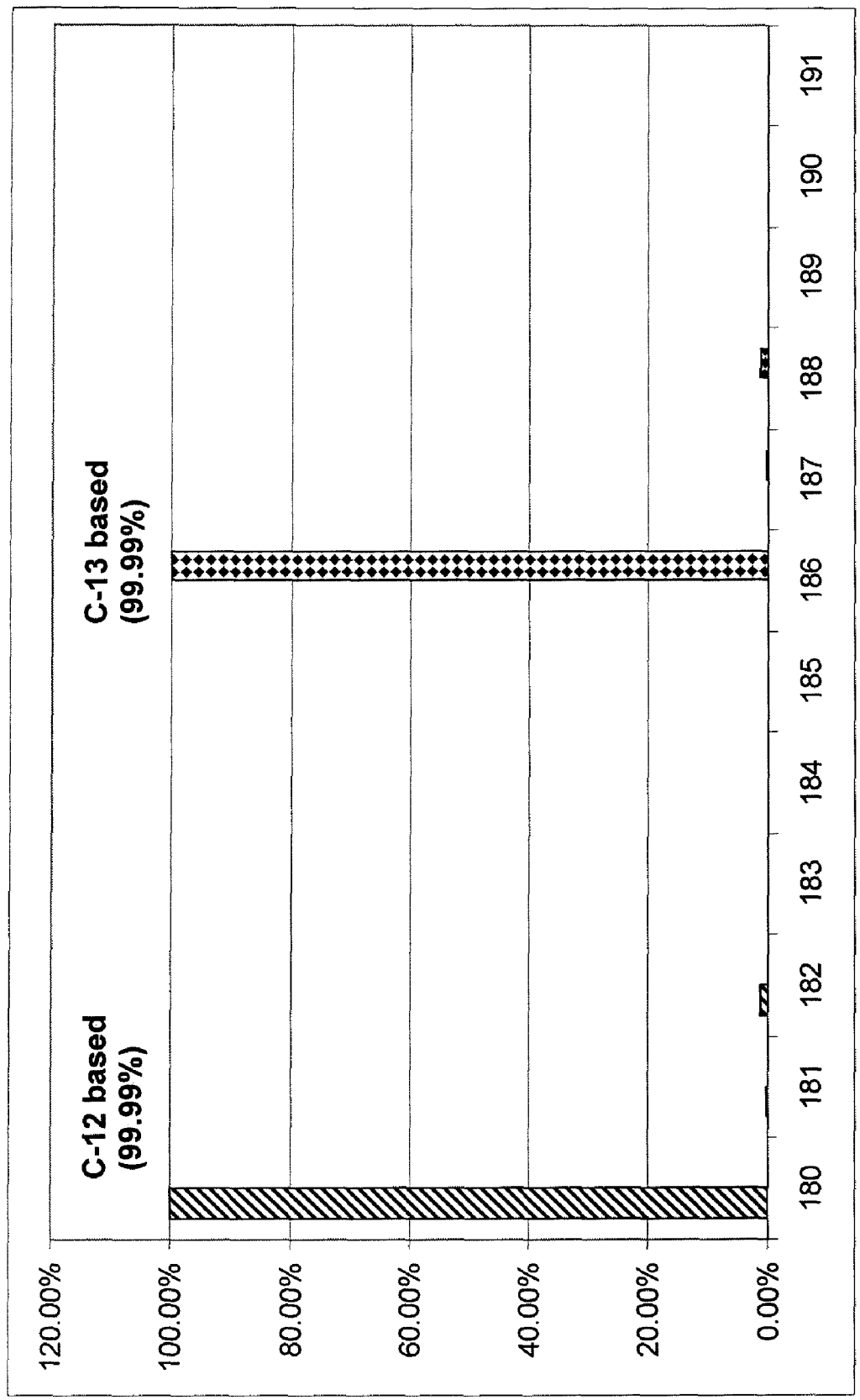
FIG. 4 illustrates a hypothetical mass spectrum obtained by mixing substantially pure (99.99%) natural C-12 glucose with an equivalent amount of substantially pure (99.99%) C-13 glucose. This situation has been considered optimal in other teachings such as WO 05059566.

Unfortunately, in a majority of biochemicals or metabolites these secondary peaks are quite small and often lost as they are indistinguishable from noise. If one were to create a similar "anti-natural abundance" for $^{13}C$; i.e., 98.9% $^{13}C$ and 1.1% $^{12}C$, then the sample would have the majority peak as the highest mass and show a number of peaks that are shifted down from it at lower masses, but again in the majority of cases these additional peaks will be indistinguishable from noise, (not shown but similar to FIG. 4), if they are detectable at all.

In the case of nearly pure isotopic starting material (see FIG. 4) the majority peak becomes even more dominant and the other peaks are even less likely to be seen. In both of the preceding cases, in a majority of the time one cannot count on seeing anything except the majority peak for each compound. Thus, in both of these cases from a composited sample, as defined above, there would be two peaks from glucose, at 180 and 186 amu, in a mass spectrum of the sample. Based on the fact that this is a known compound and previously identified, these two could be distinguished, and if the "experimental" response caused the C-13 glucose peak to drop below detectable limits then this could be determined. However, if the compound were not glucose, but rather an unknown compound and there was only one peak it would be impossible to determine if the identified peak originated from the "control" side or the "experimental".

Figure 5:
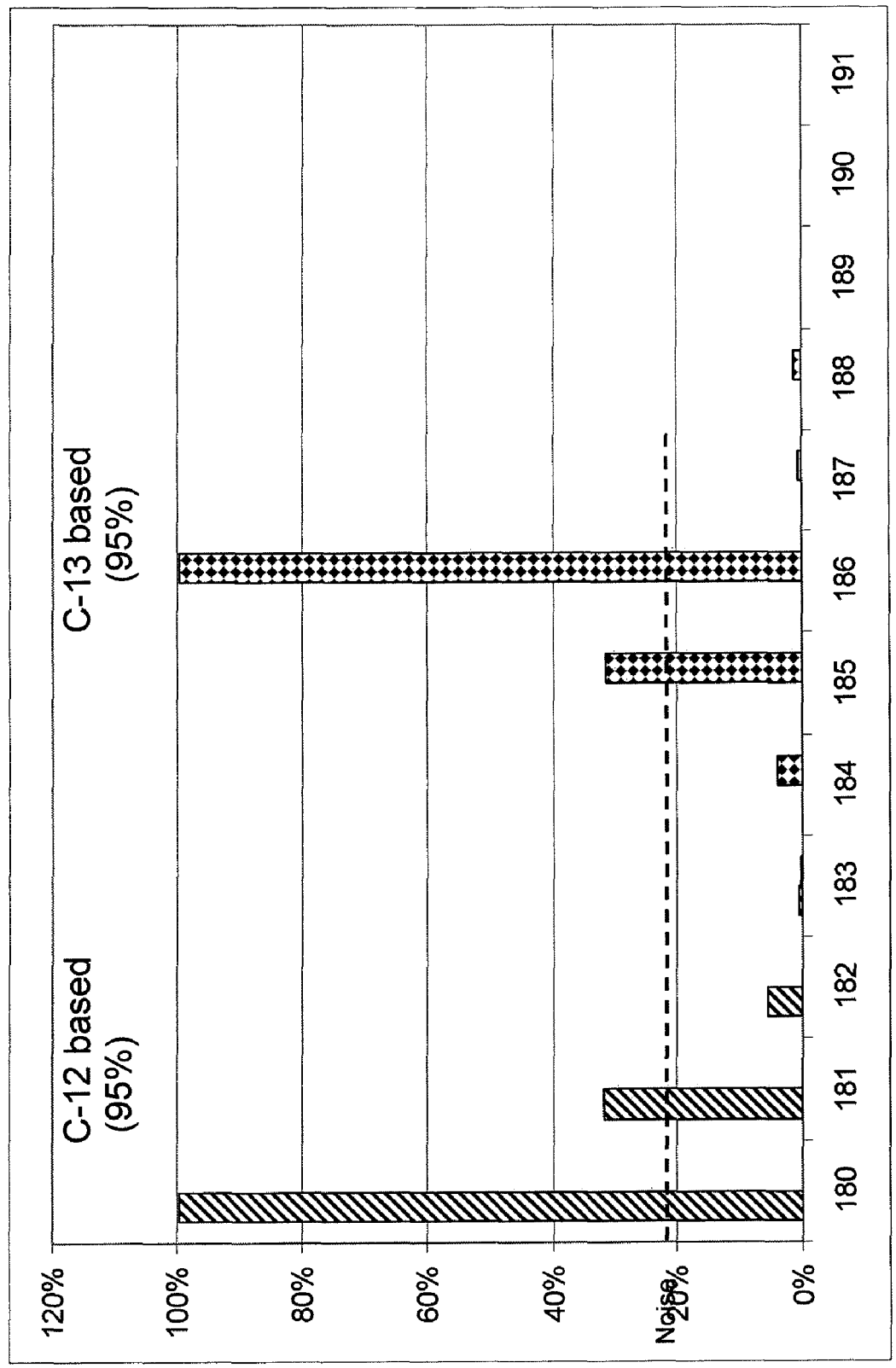
FIG. 5 illustrates a hypothetical mass spectrum for glucose showing the effects of altering the isotopic distribution on daughter ions by using non-natural abundance C-12 (95% C-12 and 5% C-13) and altered enrichment C-13 (95% C-13 and 5% C-12).

This invention improves upon this situation by specifically using material that is devised to assure that the minority peaks are present in sufficient quantity that they will generally be seen (see FIG. 5). In this case, the source of every compound can be identified because, relative to the majority peak, the minority peak will be larger in mass (and therefore derived from $^{12}C$ based cells), or the minority peak will have a smaller mass (and therefore be derived from the $^{13}C$ based cells). Thus, it is optimal to increase the percentage of the "impurity"; i.e., $^{12}C$ in $^{13}C$ or visa versa, in carefully controlled amounts significantly above their natural abundance (see Tables 1A and 1B, below).

TABLE 1A

| C-12<br>C12 + 1% | C12 + 2% | C12 + 3% | C12 + 4% | C12 + 5% | C12 + 10% | Mol. Mass |
|---|---|---|---|---|---|---|
| 1 | 1 | 1 | 1 | 1 | 1 | 180 |
| 6.43% | 12.61% | 18.92% | 25.37% | 31.95% | 67.03% | 181 |
| 1.41% | 1.90% | 2.74% | 3.93% | 5.50% | 20.00% | 182 |
| 0.08% | 0.17% | 0.30% | 0.47% | 0.70% | 3.64% | 183 |
| 0.01% | 0.01% | 0.03% | 0.04% | 0.07% | 0.48% | 184 |
| 0.00% | 0.00% | 0.00% | 0.00% | 0.01% | 0.05% | 185 |
| 0.00% | 0.00% | 0.00% | 0.00% | 0.00% | 0.00% | 186 |
| 0.00% | 0.00% | 0.00% | 0.00% | 0.00% | 0.00% | 187 |
| 0.00% | 0.00% | 0.00% | 0.00% | 0.00% | 0.00% | 188 |
| 0.00% | 0.00% | 0.00% | 0.00% | 0.00% | 0.00% | 189 |
| 0.00% | 0.00% | 0.00% | 0.00% | 0.00% | 0.00% | 190 |
| 0.00% | 0.00% | 0.00% | 0.00% | 0.00% | 0.00% | 191 |

Table 1A shows the mass profile; i.e., the isotopic distribution, for a C-12 based compound with a molecular compound of mass 180 ($C_6H_{12}O_6$) that has been diluted with various percentages of C13. Thus, a C12-based molecule of mass 180 with 95% C-12 and 5% C-13 will have an M+1 (@181 amu) that is 31.95% of the height of the parent peak at 180 amu. It will furthermore have a M+2 that is 5.5% of the parent peak. The remaining values illustrate lesser and greater dilutions of C-12 with C-13.

TABLE 1B

| C-13<br>C13 + 1% | C13 + 2% | C13 + 3% | C13 + 4% | C13 + 5% | C13 + 10% | Mol. Mass |
|---|---|---|---|---|---|---|
| 0.00% | 0.00% | 0.00% | 0.00% | 0.00% | 0.00% | 180 |
| 0.00% | 0.00% | 0.00% | 0.00% | 0.00% | 0.01% | 181 |
| 0.00% | 0.00% | 0.00% | 0.00% | 0.01% | 0.23% | 182 |
| 0.00% | 0.02% | 0.06% | 0.14% | 0.29% | 2.73% | 183 |
| 0.15% | 0.62% | 1.43% | 2.60% | 4.15% | 18.44% | 184 |
| 6.06% | 12.24% | 18.55% | 24.98% | 31.55% | 66.45% | 185 |
| 100.00% | 100.00% | 100.00% | 100.00% | 100.00% | 100.00% | 186 |
| 0.44% | 0.52% | 0.60% | 0.67% | 0.76% | 1.18% | 187 |
| 1.23% | 1.23% | 1.23% | 1.23% | 1.23% | 1.23% | 188 |
| 0.00% | 0.00% | 0.01% | 0.01% | 0.01% | 0.01% | 189 |
| 0.01% | 0.01% | 0.01% | 0.01% | 0.01% | 0.01% | 190 |
| 0.00% | 0.00% | 0.00% | 0.00% | 0.00% | 0.00% | 191 |

Conversely to Table 1A, Table 1B shows the mass profile; i.e., the isotopic distribution, for a C-13 based compound with a molecular compound of mass 186 ($C_6H_{12}O_6$) that has been diluted with various percentages of C12. Thus, a C13-based molecule of mass 186 with 95% C-13 and 5% C-12 will have an M−1 (@185 amu) that is 31.55% of the height of the parent peak at 186 amu. It will furthermore have a M−2 that is 4.15% of the parent peak. Note that this molecule will have very small M+1, etc. peaks due to isotopic contributions from other atomic species, i.e. oxygen, hydrogen, nitrogen, etc.

Therefore, the compounds that are contributed to the composite from the $^{13}C$ sample can be distinguished because they will have daughters that are at M−1 (trailing the parent), whereas those peaks from the $^{12}C$ samples will have their daughters at M+1 (leading the parent). Using this rule one can easily distinguish the source of any peak as to control or experimental.

The addition of 10% impurity ($^{13}C$ in $^{12}C$ or visa versa) results in a daughter peak that is about 66% of the size of the parent (see Tables 1A and 1B). The optimal increase over natural abundance is a function of the study in question and the average size of the molecules that the study is targeted to see, but the benefit of the augmentation of the isotopic ratios in both the $^{13}C$ and $^{12}C$ media is always a benefit.

The components of the composite sample are themselves typically separated prior to introduction into the mass spectrometer. That separation can be carried out using gas chromatography, high pressure liquid chromatography (HPLC), size exclusion chromatography, electrophoresis and the like. Various separation techniques can also be combined.

Illustrative equipment that can be used to carry out a contemplated method include the following.

Mass Spectrometers: Agilent 6520 Accurate-Mass Q-TOF LC/MS, Agilent 5975 Series MSD, Thermo-Fisher LTQ, Thermo-Fisher ORBITRAP®, Waters MICROMASS® GCT Premier™, and Waters LCT Premier™.

Separation systems can be part of the MS (as in GC) or separate, and illustratively include: Waters ACQUITY UPLC®, Agilent Rapid Resolution, and Thermo Surveyor Plus systems.

The two other major classes of compounds found in any sample, namely artifacts, and introduced compounds, can now be examined. In the case of artifacts, the material necessarily exhibits a natural abundance isotopic distribution. If the biological compounds derived from biological sources were developed on media containing non-natural distributions of isotopes, the ability to discriminate artifacts becomes quite easy based on the size of the daughter peaks. On the other hand, for compounds that are exogenously introduced as an experimental variable, as drugs, medicines, toxins, or the like, it is likely that they will participate to some extent in the biological processes. Therefore, if they are synthesized using highly enriched $^{13}C$, they will not have the significant daughters of the normal biological components and thus can be distinguished. Even after these exogenous compounds have undergone significant biological transformation, their daughter ions will have lower than normal ratios allowing them to be identified as derivatives of the exogenously applied compounds.

The above observations permit one to classify distinctive patterns that are important in the interpretation of the resulting composite spectra. Because one can discriminate which portion of the study; i.e., $^{12}C$ or $^{13}C$, artifact or derivative of an exogenously applied compound, every peak in the composite comes from, one can interpret the analytical results of the composite sample to an even greater extent. These expectations are easily reduced to appropriate software, and thus this process can be fully automated.

Ion suppression is a phenomenon that occurs during the mass spectroscopic ionization processes when the efficiency of ionization is subjected to variability due to characteristics of the compounds that are present. Thus, in its most common form, the number of molecules that could be ionized is in excess of the amount of charge available. In this situation the molecules that become ionized most efficiently are those that can acquire the charge most strongly, and the remaining molecules become ionized with much lower efficiency.

The variability introduced here makes the quantification of these molecules very poor. The present method side-steps this issue completely. Because every compound is found in both control and experimental compositions, with each being represented by two isotopomeric equivalents, and for every compound both compounds are internal to the same sample and have nearly identical chemical properties, then both will be subject to exactly the same ion suppression inefficiencies.

Under this scenario the ratio of one to the other is a true reflection of their relative concentrations in the original sample irrespective of anything except 100% ion suppression, which rarely occurs. In the vast majority of cases very valuable information has been recovered that would otherwise have been lost or of suspect quantification.

ILLUSTRATIVE EXAMPLE

A general description of the method is illustrated by a study in which:

1. A single homogeneous collection of living organisms (it can be a cell culture of animal, bacterial, fungal or of plant cells, and can be actively growing or in a suspended, but revivable, state, or even whole organisms), 2. is subjected to one or more wash/rinse cycle(s) using a biologically neutral buffer, 3. is re-suspended in the same buffer and apportioned in such a way as to create a number of samples that they have an equal or approximately equal number of cells or organisms.

4. The buffer is removed (by centrifugation, filtration or other means).

5. Two identical media are prepared, in one (herein called "C12 media") all carbon sources (sugars, lipids, amino acids, proteins, etc) contain only isotopically enriched $^{12}C$ (i.e., enhanced by addition of $^{13}C$), and in the other (herein called "C13 media"), all the carbon sources are isotopically enriched $^{13}C$ enhanced with a comparable percentage of $^{12}C$.

6. Wash (as in step 2) one-half of the samples one or more times with the C12 medium and the other half of the samples should be equally treated with the C13 medium.

7. After the final wash, dispense the cells to a vessel suitable for growth and in which the only medium available is either the C12 or C13 medium in which the cells were last washed.

8. By performing the above steps, one should end up with two sets of identical cultures, all of which have approximately the same number of the statistically similar cells, but half of which use C12 medium for growth (herein referred to as "C12 samples") and the remainder use C13 medium for growth (herein referred to as "C13 samples"). For purposes of this illustration, the C12 samples are deemed to receive the control and the C13 samples are deemed to receive the stressor, although in practice this can be reversed. What is important is that the samples be handled so that for each C13 sample there is an equivalent C12 sample.

9. Both sets of samples are permitted to grow out for a number of cell division cycles before proceeding. (This growth will dilute any of the original isotopes that may inadvertently have been carried in at the start of this study by the original cells.)

10. After an appropriate growth period, one of the test systems (here arbitrarily, C13) should receive treatment with the stressor (drug, toxin, physical, physiological or other), while the other (C12) gets an identical placebo or control treatment.

11. After an appropriate period for the stressor to act, the cells/organisms are harvested and the samples are matched up. The C13 (stressor-treated) and the C12 (control or placebo treated) matched samples are combined during the harvest process to create a single composite sample.

12. A detailed analysis (metabolomic, proteomic, transcriptomic, or analysis for any other carbon-based class of compounds) can be performed on the composite samples:

a) the relative C12/C13 ratios of the analytes (of known or unknown identity) are determined, b) statistical variance of the ratios is determined, c) an analyte compound that has a ratio that is a significant deviation from the average ratio indicates a point where the biochemistry was altered. For instance, if the average ratio for the all of the analytes is 1 (1:1 C12/C13 ratio), but some analytes have ratios of 10 (10:1) or 0.1 (1:10), then the analytes that are outliers to the general population are those most strongly effected by the stressor.

The above method easily supersedes current methods in which individual samples representing the different populations, but not isotopically defined, are used. The benefits of this method include:

1. The ability to prepare and label composite samples. The composite sample is statistically derived from a single homogeneous cell mass, grown, treated, and harvested under nearly identical conditions, and prepared and analyzed under identical conditions. Experimentally, the major source of biological variance is the treatment with the stressor.

2. Abnormalities are seen by looking for outliers; i.e., deviations in the ratios of the $^{12}C$ to $^{13}C$ ratios for every desired analyte/compound within the sample.

3. The process does not require that the identity of an analyte/compound be known to understand that its biochemical environment has been effected.

4. A smaller number of samples are required to be analyzed in order to determine any outcome because the artifactual noise inherent in the experiment is reduced.

5. Although the method can applied to situations where the cells are actively dividing, it can also be applied to any situation in which the cells are metabolically active.

6. Artifacts can be identified as analyte compounds that are not seen as paired in either control or experimental samples, and demonstrate a "normal" isotopic distribution.

7. Within this method, exogenous compounds and their biochemical derivatives can be identified and tracked when they are given an isotopic distribution that is different from the media isotopic distributions.

A contemplated method relies on establishing a set of relationships within a single sample that is to be analyzed. Because of the predictable form these relationships take, the entire method can be reduced to a set of algorithms that can be coded in software. This software performs these functions in an automated manner, and produces a data set that details 1) analyte compounds found in the sample, 2) the $^{12}C/^{13}C$ ratios for those analyte compounds, 3) the relevance of the compound to the response profile, 4) non-biological artifacts, and 5) derivatives of exogenously applied compounds.

At its most fundamental the methods described impose patterns in the final data set that can be used in the interpretation of the data set to achieve a greater degree of precision, and accuracy than can be achieved by any other method. However, it is one thing to create these patterns, and another to use them.

The software that is required in their use must be aware of the nature of the patterns created and then seek them in the final data set. In one such application, a composite sample is provided and is subjected to a separation phase, such as a GC, HPLC or other chromatographic separation. The effluent of the separation is then analyzed by mass spectroscopy. The patterns are buried in the raw mass spectrometer data set as a series of scans with each scan representing a sequential time segment.

The algorithm used to seek the patterns can take many forms; however, in one instance 1) all of the ions seen by the mass spectrometer at a single point in time (scan, or possibly a de-convoluted peak) are gathered into a subset;

2) the analyte ions in this subset are initially sorted by their m/z values, and then are then resorted based on their height or amplitude;

3) the pattern of ions (from top to bottom) is examined to determine where the slope of the ion trace becomes approximately level. This point defines random noise, and all further ions are considered "noise". Noise ions are removed from consideration.

4) Starting from the ions with the greatest height or amplitude, the individual ions are examined (queried by the software) sequentially:

a) For each ion (that has m/z or mass of M)

i. Does the M+1 have the size compatible with its being based on a C-12 majority molecule; i.e., with 3% to 10% C-13 overall incorporation? In this situation, the M+1 will be between 18%, 31%, or 66% if the molecule has a mass of approximately 180 and has 3%, 5%, or 10% C-13 content, respectively. If so, the analyte ion is identified as a C-12 majority molecule and all associated ions (M+1, M+2, etc.; similarly identified) are removed from future consideration. The next highest available analyte ion is then examined.

ii. Does the M−1 have the size compatible with its being based on a C-13 majority molecule; i.e., with 3% to 10% C-12 overall incorporation? In this situation, the M−1 will be between 18%, 31%, or 66%, respectively, if the molecule has a mass of approximately 180 and has 3%, 5%, or 10% C-13 content. If so, this analyte is identified as a C-13 majority molecule and all associated ions (M−1, M−2, etc.; similarly identified) are removed from future consideration. The next highest available ion is thereafter examined.

iii. Does the M+2 demonstrate a pattern associated with a standard? If so, it is identified as a standard and all associated ions (M+2, etc.) are removed from future consideration. The next highest available analyte ion is thereafter examined.

iv. If none of the above are true, the analyte ion is derived from an artifact and not experimentally significant. It is removed from further consideration.

b) This process is repeated until all analyte ions at this time point (and not yet accounted for) are analyzed.

5) Steps 1 to 4 will be repeated for all time points.

6) The outcome of the above process identifies all analyte ions as either derived from a C-12 majority molecule, a C-13 majority molecule, a standard or removes them from consideration.

a) All analyte ions are now grouped in time to form peaks (if this has not already been done. In other manifestations this can be done in an earlier stage.) These peak characteristics include a start time, end time, maximal time, base mass, maximal height of base ion, etc.)

b) For all C-12 majority molecules, a matching C-13 majority molecule is sought. This matching molecule demonstrates a similar time signature; i.e., similar start time, end time, and maximal time. Values to collect include:

i. The mass difference between the C-12 majority base mass and the C13 majority base mass represents the number of carbons in the molecule.

ii. The ratio between the maximal height of the C-12 majority molecule and the maximal height of the C13 majority molecule.

c) For all standards, their time is noted.

7) Alignment of all pairs can be accomplished by standard methods for calculating or normalizing retention indices (illustratively by use of the internal standards).

8) The mean and standard deviation for the ratio values for all pairs is calculated.

9) All pairs that deviate outlier ratios are identified by evaluation of their deviation from the mean. This final step of the evaluation can vary according to experimental design and analytical conditions.

There are many possible ways of rearranging the steps described here or accomplishing each of their outcome but they all will need to accomplish the majority of the above steps.

A contemplated method is general in its applicability and is illustrated by the following specific examples.

1. A bacterial cell response to a stressor that is an antibacterial drug

A. Time Course of Drug Response-

In this instance the experimental design is set up in order to determine the effect of a drug on bacterial cultures as a function of time. In this instance, because of the nature of the question to be answered, the appropriate control is a contemporaneous culture.

An actively growing culture of a *Escherichia coli* (bacteria) is subjected to one or more wash/rinse cycle(s) using an isotonic but non-nutritional (IN) buffer (via centrifugation). The resulting pellet of cells is re-suspended in the same IN buffer and apportioned to create 24 samples that they have an equal or approximately equal number of bacterial cells.

The IN buffer is removed from these 24 samples. Two identical media are prepared, in one (herein called "C13 medium") the sole carbon source is isotopically enriched $^{13}$C-glucose (as discussed above), and in the other (herein called "C12 medium") the sole carbon sources is isotopically enriched $^{12}$C-glucose (as discussed above).

Twelve of the samples are washed three times with the C12 medium and the remaining 12 samples are similarly washed with the C13 medium. After the final wash, the cells are dispensed into a vessel suitable for growth and in which the only medium available is either the C12 or C13 medium in which the cells were last washed.

By performing the above steps, one prepares two sets of 12 identical cultures, each of which has approximately the same number of the statistically similar cells, but half of which use C12 medium for growth (herein referred to as "C12 samples") and the remainder use C13 medium for growth (herein referred to as "C13 samples"). For purposes of this illustration, the C12 samples are deemed to receive the control and the C13 samples receive the stressor, although in practice this can be reversed. The important point is that the samples be handled so that for each C13 sample there is an equivalent C12 sample.

Both sets of samples are grown until they reach exponential growth and have undergone several cellular divisions. After the appropriate growth period the 12 C13 samples receive treatment with a stressor such as an antibacterial drug, whereas the C12 samples receive an identical placebo or control treatment.

After an appropriate period for the stressor/drug to act, the cells/organisms are harvested and the samples are matched up. The C13 (stressor treated) and the C12 (control or placebo treated) matched samples are combined during the harvest process to create a single composite sample. In this example three composites can be created at time 0, 1, 4, and 24 hours, respectively.

A detailed analysis (metabolomic, proteomic, transcriptomic, or analysis for any other carbon-based class of compounds) is performed on the composite samples.

The relative C12/C13 ratios of the analytes of each sample (of known or unknown identity) are determined. The statistical variance of the ratios sample is determined.

An analyte compound that has a C12/C13 ratio that is a significant deviation (two or more standard deviations) from the average ratio is indicative of a point at which the biochemistry was altered. For example, if the average ratio for the analytes is 1 (1:1 C12/C13 ratio), but some analytes have ratios of 10 (10:1) or 0.1 (1:10) then the analytes that are outliers to the general population, e.g., those with ratios of 10 and 0.1, are those most strongly effected by the stressor and indicate a point of biochemical alteration.

B. Time Course of Drug Response

In this instance, the experimental design is set up in order to determine the effect of a drug on mammalian cell cultures as a function of time. In this instance, because of the nature of the question to be answered, the appropriate control is a contemporaneous culture.

An actively growing culture of human hepatocytes is subjected to one or more wash/rinse cycle(s) using an isotonic but non-nutritional (IN) buffer (via centrifugation). The resulting pellet of cells is re-suspended in the same IN buffer and apportioned in such a way as to create 24 samples that they have an equal or approximately equal number of bacterial cells. The IN buffer is removed from these 24 samples.

Two identical media are prepared, in one (herein called "C13 medium") the sole carbon source is isotopically enriched $^{13}C$-glucose (as discussed above), and in the other (herein called "C12 medium") the sole carbon sources is isotopically enriched $^{12}C$-glucose (as discussed above). (An exemplary medium is Williams Medium E, a fully defined medium capable of supporting growth for extended periods of time or any other medium that can be isotopically defined.)

Twelve of the samples are washed three times with the C12 medium and the remaining 12 samples are similarly washed with the C13 medium. After the final wash, the cells are dispensed into a vessel suitable for growth and in which the only growth nutrient-containing medium available is either the C12 or C13 medium in which the cells were last washed.

By performing the above steps, one prepares two sets of 12 identical cultures, each of which has approximately the same number of the statistically similar cells, but half of which use C12 medium for growth (herein referred to as "C12 samples") and the remainder use C13 medium for growth (herein referred to as "C13 samples"). For purposes of this illustration, the C12 samples are deemed to receive the control and the C13 samples receive the stressor, although in practice this can be reversed. The important point is that the samples be handled so that there is an equivalent C12 sample for each C13 sample from which a data point is desired.

Both sets of samples are permitted to grow (metabolize in situ if not dividing) until they have attained a desired isotopic replacement. In the case of a dividing cell it can have undergone several cellular divisions. After the appropriate growth period, the 12 C13 samples receive treatment with a stressor such as a drug (atorvastatin calcium), drug candidate, or another compound for which the biochemical response is sought, whereas the other C12 samples receive an identical placebo or control treatment.

After a further appropriate time period for the stressor to act, the cells are harvested and the samples are matched up. The C13 (stressor treated) and the C12 (control or placebo treated) matched samples are combined during the harvest process to create a single composite sample. In this example three composites may be created at time 0, 1, 4, and 24 hours, respectively.

A detailed analysis (metabolomic, proteomic, transcriptomic, or analysis for any other carbon-based class of compounds) is performed on the composite samples. The relative C12/C13 ratios of the analytes of each sample (of known or unknown identity) are determined. The statistical variance of the ratios sample is determined.

An analyte compound that has a C12/C13 ratio that is a significant deviation (two or more standard deviations) from the average ratio indicates a point at which the biochemistry was altered, as discussed previously. For example, if the average ratio for the analytes is 1 (1:1 C12/C13 ratio), but some analytes have ratios of 10 (10:1) or 0.1 (1:10) then the analytes that are outliers to the general population, e.g., those with ratios of 10 and 0.1, are those most strongly effected by the stressor and indicate a point of biochemical alteration.

C. Growth Curves or Effect of Age

In this instance, the point of comparison is time zero. In this instance the experimental design is set up in order to determine the effect of aging on cell cultures. Because of the nature of the question to be answered, the appropriate control is an aliquot of the time zero culture, which here is one hour after the application of fresh medium.

An actively growing culture of a mammalian primary cell line is subjected to one or more wash/rinse cycle(s) using an isotonic but non-nutritional (IN) buffer (via centrifugation). The resulting pellet of cells is re-suspended in the same IN buffer and apportioned in such a way as to create 24 samples that they have an equal or approximately equal number of cells. The IN buffer is removed from these 24 samples.

Two identical media are prepared. In one (herein called "C12 medium"), the sole carbon source is isotopically enriched (as defined in the above), $^{12}C$-glucose, and an appropriate collection of equally enriched $^{12}C$-amino acids and other nutrients. In the other (herein called "C13 medium"), the sole carbon sources are similarly isotopically enriched but with $^{13}C$ compounds.

Twelve of the samples are washed three times with the C12 medium and the remaining 12 samples should be equally treated with the C13 medium. After the final wash, the cells are dispensed into a vessel suitable for growth and in which the only nutrient-containing medium available is either the C12 or C13 medium in which the cells were last washed.

One should have two sets of 12 identical cultures, all of which have approximately the same number of the statistically similar cells, but half of which use C12 medium for growth (herein referred to as "C12 samples"), and the remainder use C13 medium for growth (herein referred to as "C13 samples"). For purposes of this illustration, the C12 samples are the control cultures and the C13 samples are the samples which are permitted to age, although in practice this can be reversed. The important point is that the samples be handled so that there is an equivalent C12 sample for each C13 sample from which a data point is desired. Both sets of samples are permitted to grow until such time that they have diluted all pre-existing or native carbon with medium-supplied carbon isotopes. If the cells are dividing they should undergo several cellular divisions.

After the appropriate growth period, the C13 samples have their medium removed and replaced with fresh C13 medium. The C12 samples are similarly treated and also be given fresh medium. This can be considered time t=−1 Hr. After a further one hour period has passed (T=0), all of the aliquots of the C12 medium cells (designated controls) are individually harvested and frozen. Three of the C13 (aging) cultures are harvested at time (T=0) and added to their matched 12C harvested aliquots. Additional triplicate sets of the aging cells are harvested at T=24, T=48, T=120 hours. As these cells are harvested they are paired with their matched T=0 samples to create composite samples.

A detailed analysis (metabolomic, proteomic, transcriptomic, or analysis for any other carbon-based class of compounds) is performed on the composite samples. The relative C12/C13 ratios of analytes per sample (of known or unknown identity) are determined. The statistical variance of the ratios sample is determined.

Any analyte compound that has a ratio that is a significant deviation (two standard deviations or more) from the average ratio will indicate a point where the biochemistry was altered. For instance, if the average ratio for the all of the analytes is 1 (1:1 C12/C13 ratio), but some analytes have ratios of 10 (10:1) or 0.1 (1:10) then the analytes that are outliers to the general population are those most strongly effected by the stressor.

D. Growth Curves or Effect of Age in a Multicellular Eukaryotic Organism

In this instance, the experimental point of comparison is time zero in a whole organism. The experimental design is set up in order to determine the effect of aging on an animal, for illustration here the nematode, *Caenorhabditis elegans*. Because of the nature of the question to be answered, the appropriate control is an aliquot of the time zero organism, which in this instance is one hour after the application of second round of fresh media. The stressor and stress regimen here is aging and growth of the organism during aging.

An actively growing culture of a *C. elegans* and its feedstock of is subjected to one or more wash/rinse cycle(s) using an isotonic but non-nutritional (IN) buffer (via centrifugation). The resulting pellet of nematodes is re-suspended in the same IN buffer and apportioned in such a way as to create 2 samples, each of which has an equal or approximately equal number of nematodes. The IN buffer is removed from these 2 samples.

Two identical media are prepared. In one (herein called "C12 medium"), the sole carbon source is isotopically enriched $^{12}$C-glucose (upon which the bacterial feedstock of the nematode grow), and in the other (herein called "C13 medium") the sole carbon sources is isotopically highly enriched $^{13}$C-glucose.

One of the samples is washed three times with the C12 medium and the remaining sample is equally treated with the C13 medium. After the final wash, the nematodes are dispensed into a vessel suitable for growth and in which the only nutrient-containing medium available is either the C12 or C13 medium in which the cells were last washed.

Two identical *C. elegans* cultures, both of which have approximately the same number of organisms are thus prepared. One of the cultures uses C12 medium for growth (herein referred to as "C12 samples") and the other uses C13 medium for growth (herein referred to as "C13 samples").

(For purposes of this illustration, the C12 sample is the control culture and the C13 sample is the sample that is permitted to age, although in practice this can be reversed. The important point is that the samples be handled so that there is an equivalent C12 sample for the C13 sample. Both samples should be permitted to grow until they reach exponential growth and have undergone at least 1 or 2 full generations. After the appropriate growth period, the C13 sample has its medium removed and replaced with fresh C13 medium. The C12 sample is similarly treated and also be given fresh medium.

After the appropriate subsequent growth period, the C13 sample should have its medium removed and replaced with fresh C13 medium and the nematodes separated for age. Only the youngest stage is permitted to proceed. The C12 sample is similarly treated and also be given fresh medium.

After a one hour period has passed (T=0), the C12 culture is aliquotted to 24 equal portions and nematodes in each aliquot harvested and frozen (as the controls). Three of the C13 (aging) cultures are similarly harvested at time (T=0) and the harvested nematodes added to their matched 12C harvested controls. Additional triplicate sets of the aging cells are harvested at T=24, T=48, T=120. As these nematodes are harvested they are paired with their matched T=0 samples to create the composite samples.

A detailed analysis (metabolomic, proteomic, transcriptomic, or analysis for any other carbon-based class of compounds) is performed on the composite samples. The relative C12/C13 ratios of analytes per sample (of known or unknown identity) are determined. The statistical variance of the ratios sample is determined.

Any analyte compound that has a ratio that is a significant deviation (two or more standard deviations) from the average ratio will indicate a point where the biochemistry was altered. For instance, if the average ratio for the all of the analytes is 1 (1:1 C12/C13 ratio), but some analytes have ratios of 10 (10:1) or 0.1 (1:10) then the analytes that are outliers to the general population are those most strongly effected by the stressor.

E. Functional Alterations of Gene Manipulations in Plants

The experimental point of comparison here is a wild type organism. In this instance, the experimental design is set up to determine the effect of genetic manipulation upon the mustard, *Arabidopsis thaliana*. Because of the nature of the question to be answered, appropriate control is an aliquot of the genetically unmodified, or wild-type plant, which may be prepared separately from the experimental samples, but which needs to be from a single homogeneous control.

The genetically modified plants are preferably derived from a common and consistent wild type background. For this illustration, it is presumed that there are one or more such genetically modified plants (arbitrarily, 5) genetically distinct clones, all of which were derived from the same wild type stock. All of these genetically modified plants are stored as fresh viable seed at the start of the study.

A large collection of wild type seeds are grown under controlled conditions in an atmosphere of isotopically enriched $^{13}$C-carbon dioxide ($CO_2$) as defined above. These plants are harvested in a manner appropriate to the experimental design, illustratively at maturity. Sufficient control sample can be prepared at one time for more than one study; i.e., all of the control plants should be combined into a single homogeneous sample.

The plants are harvested by direct immersion into liquid nitrogen and subsequently stored at −80° C. The frozen plants are powdered while in the frozen state.

The genetically modified (GMO) seed is grown in a manner similar to that above, but these plants are grown under identical conditions except that their carbon source is carbon dioxide having an inverted $^{12}C/^{13}C$ ratio. These GMO plants are harvested according to the protocol used above, and powdered as before. In the case of the GMO samples, each sample is harvested and treated individually. Equal aliquots of the control powder are added to equal aliquots of the GMO experimental powders to form the composite samples.

A detailed analysis (metabolomic, proteomic, transcriptomic, or analysis for any other carbon-based class of compounds) is performed on the composite samples. The relative C12/C13 ratios of analytes per sample (of known or unknown identity) are determined. The statistical variance of the ratios sample is determined.

Any analyte compound that has a ratio that is a significant deviation (two or more standard deviations) from the average ratio will indicate a point where the biochemistry was altered. For instance, if the average ratio for the all of the analytes is 1 (1:1 C12/C13 ratio), but some analytes have ratios of 10 (10:1) or 0.1 (1:10) then the analytes that are outliers to the general population are those most strongly effected by the stressor.

F. Physiological Stress in a Rat

Higher organisms represent a special case. In this instance, the experimental point of comparison is a whole higher organism and therefore one in which the concept of the experimental and control sample becomes more complicated as the biological variance within the test population is rather large. This can necessitate the compositing of individual samples to form "biologically averaged" Experimental and Control samples. These averaged samples are then composited.

In this example the experimental design is set up to determine the effect of physiological stress (induced by fasting for 24 hours) on an animal, for illustration here the rat, *Rattus norvegiensus*. Because of the nature of the question to be answered, the appropriate control is a composite sample of rat plasma and the experimental sample is a composite sample of rat plasma from rats that have undergone the experimental, stressing treatment, which in this example will be starvation for 24 hours.

Due to the nature of the experiment it is expedient that the control population is the C-13 animal as the control need not be contemporaneous and can be a standard control that is available prior to the actual running of the experiment. Because the test system has animals, the experiment has more noise due to the greater variance inherent in the source material. The use of sample compositing partially offsets this problem as it averages the inherent biological variability, thus rendering the samples more representative of the norm. This results in a simplified experimental design, although it requires more complex prior preparation.

A group of rats ("the experimental population") of a defined strain are placed on a defined isotopically enriched C-12 diet from birth. Meanwhile another group of rats ("the control population"), of the same strain (although possibly at a different point in time) are grown on the C-13 equivalent diet. Both groups of animals are grown under identical environmental conditions.

At the age of 6 weeks, the experimental animals are subjected to the experimental condition, for illustration here fasting for 24 hours beginning at the time that the light-cycle starts. Therefore the experimental samples, plasma samples, are taken at the beginning of the light cycle on the following day.

All of the samples from the experimental group are similarly collected. A composite experimental sample is created by mixing equal aliquots of plasma from all experimental animals. The control samples are similarly collected and composited from animals that have been feed a C-13 equivalent diet.

By performing the above manipulations, one obtains two similar samples that contain the required information content, namely the definition of the experimental response condition and the definition of the control condition. This creates the pair of samples to be mixed to create the composite sample for analysis.

A detailed analysis (metabolomic, proteomic, transcriptomic, or analysis for any other carbon-based class of compounds) is performed on the composite samples. The relative C12/C13 ratios of analytes per sample (of known or unknown identity) are determined. The statistical variance of the ratios sample is determined.

Any analyte compound which has a ratio that is a significant deviation (two or more standard deviations) from the average ratio will indicate a point where the biochemistry was altered. For instance, if the average ratio for the all of the analytes is 1 (1:1 C12/C13 ratio), but some analytes have ratios of 10 (10:1) or 0.1 (1:10) then the analytes that are outliers to the general population are those most strongly effected by the stressor.

Each of the patents and articles cited herein is incorporated by reference. The use of the article "a" or "an" is intended to include one or more.

The foregoing description and the examples are intended as illustrative and are not to be taken as limiting. Still other variations within the spirit and scope of this invention are possible and will readily present themselves to those skilled in the art.

The invention claimed is:

1. A method for identifying an analyte of a biological sample that is affected by a stressor comprising the steps of:
   (a) providing a composite biological organism sample that is comprised of two admixed substantially identical samples of biological organisms that are a control sample and an experimental sample, wherein said control sample organisms had been grown in a first nutrient medium containing predetermined amounts of first and second isotopes of a first atom within a nutrient, and said experimental sample was grown in a second nutrient medium substantially identical to said first nutrient medium but containing different predetermined amounts of said first and second isotopes of said first atom within said nutrient compared to said first nutrient medium, said first and second isotopes being other than H or D, said experimental sample being cultured with stressing regimen containing a stressing agent for a time period sufficient for said sample to grow and said control sample being cultured for the same period of time with a regimen substantially identical to the stressing regimen but lacking the stressing agent and maintaining said regimen;
   (b) mass spectroscopically analyzing said composite biological organism sample for analyte peaks;
   (c) determining the ratio of first isotope to second isotope for each analyzed analyte peak;
   (d) determining the composite biological organism sample median isotopic ratio; and
   (e) comparing the ratio of first isotope to second isotope for each analyzed analyte peak with the composite biological sample median isotopic ratio, an analyte whose isotopic ratio significantly deviates from the composite biological sample median isotopic ratio being an analyte affected by the stressing agent.

2. The method according to claim 1, wherein said first and second isotopes of said first atom are selected from the group consisting of $^{12}$C and $^{13}$C, $^{16}$O, $^{17}$O and $^{18}$O, $^{14}$N and $^{15}$N, $^{32}$S, $^{33}$S, $^{34}$S and $^{36}$S, $^{35}$Cl and $^{37}$Cl, $^{24}$Mg, $^{25}$Mg and $^{26}$Mg, $^{27}$Si, $^{28}$Si and $^{29}$Si, $^{40}$Ca, $^{42}$Ca, $^{43}$Ca, and $^{44}$Ca, and $^{79}$Br and $^{81}$Br.

3. The method according to claim 1, wherein said first and second nutrient media further contain predetermined amounts of first and second isotopes of a second atom within a nutrient.

4. The method according to claim 1, wherein said biological organism sample is a cell culture.

5. A method for identifying an analyte of a biological organism sample that is affected by a stressor comprising the steps of:
  (a) providing two substantially identical biological organism samples, the first sample being a control sample and the second sample being an experimental sample, said control sample organisms having been conditioned in a first nutrient medium containing predetermined amounts of first and second isotopes of a first atom within a nutrient, and said experimental sample having been conditioned in a second nutrient medium substantially identical to said first nutrient medium but containing different predetermined amounts of said first and second isotopes of said first atom within said nutrient compared to said first nutrient medium, said first and second isotopes being other than H or D;
  (b) growing the experimental sample in said second nutrient medium with a stressing regimen containing a stressing agent and maintaining said stressing regimen for a time period sufficient for said experimental sample to grow;
  (c) growing the control sample in said first nutrient medium with a regimen substantially identical to the stressing regimen but lacking the stressing agent and maintaining said regimen for a time period sufficient for said control sample to grow;
  (d) admixing the two samples to form a composite biological sample;
  (e) mass spectroscopically analyzing said composite biological sample for analyte peaks;
  (f) determining the ratio of first isotope to second isotope for each analyzed analyte peak;
  (g) determining the composite biological sample median isotopic ratio; and
  (h) comparing the ratio of first isotope to second isotope for each analyzed analyte peak with the composite biological sample median isotopic ratio, an analyte whose isotopic ratio significantly deviates from the composite biological sample median isotopic ratio being an analyte affected by the stressing agent.

6. The method according to claim 5, wherein said biological sample is a cell culture.

7. The method according to claim 6 wherein said cell culture is comprised of plant cells.

8. The method according to claim 7, wherein said plant cells are algal cells.

9. The method according to claim 7, wherein said plant cells are higher plant cells.

10. The method according to claim 6, wherein said cell culture is comprised of yeast cells.

11. The method according to claim 6, wherein said cell culture is comprised of animal cells.

12. The method according to claim 6, wherein said nutrient is selected from the group consisting of a saccharide, an amino acid and a salt.

13. The method according to claim 12, wherein said first and second isotopes are selected from the group consisting of $^{12}$C and $^{13}$C, $^{16}$O, $^{17}$O and $^{18}$O, $^{14}$N and $^{15}$N, $^{32}$S, $^{33}$S, $^{34}$S and $^{36}$S, $^{35}$Cl and $^{37}$Cl, $^{24}$Mg, $^{25}$Mg and $^{26}$Mg, $^{27}$Si, $^{28}$Si and $^{29}$Si, $^{40}$Ca, $^{42}$Ca, $^{43}$Ca, and $^{44}$Ca, and $^{79}$Br and $^{81}$Br.

14. The method according to claim 5, wherein said samples admixed in step (d) are admixed in substantially equal amounts.

15. The method according to claim 5, wherein the ratio of first isotope to second isotope is analyzed for fewer than all analyte peaks.

16. The method according to claim 5, wherein the analyte peaks for which said composite biological sample is analyzed are selected from the group consisting of metabolites, saccharides, polypeptides, glycopeptides, polynucleotides, and mixtures thereof.

* * * * *